United States Patent [19]

Oshefsky et al.

[11] Patent Number: 4,863,542

[45] Date of Patent: Sep. 5, 1989

[54] METHOD AND APPARATUS FOR APPLYING DISCREET ELASTIC STRIPS TO A STATIONARY WEB

[75] Inventors: Daniel J. Oshefsky; Gregory J. Rajala, both of Neenah, Wis.

[73] Assignee: Kimberly-Clark Corporation, Neenah, Wis.

[21] Appl. No.: 145,850

[22] Filed: Jan. 19, 1988

[51] Int. Cl.[4] ............................................. B32B 31/16
[52] U.S. Cl. .................................... 156/160; 156/73.1; 156/230; 156/303; 156/495; 156/519; 156/552; 156/164
[58] Field of Search ............. 156/73.1, 160, 161, 156/164, 229, 285, 302, 382, 494, 495, 497, 519, 517, 552, 571, 574, 230, 303, 469, 553, 581

[56] References Cited

U.S. PATENT DOCUMENTS

| | | | |
|---|---|---|---|
| 4,083,737 | 4/1978 | Foote, Jr. et al. | 156/73.1 |
| 4,284,454 | 8/1981 | Joa | 156/163 |
| 4,323,409 | 4/1981 | Alt | 156/519 X |
| 4,617,082 | 10/1986 | Oshefsky et al. | 156/164 X |
| 4,675,068 | 6/1987 | Lundmark | 156/495 |
| 4,726,874 | 2/1988 | Van Vliet | 156/495 |
| 4,726,876 | 2/1988 | Tomsovic | 156/552 |

Primary Examiner—David Simmons
Assistant Examiner—David W. Herb
Attorney, Agent, or Firm—John L. Chiatalas

[57] ABSTRACT

An apparatus (10) for applying an elastic material (14) to a backing material (18) includes an applicator assembly (12) for applying a length of elastic material (14) to a bonding template (16), and a bonding template (16) for supporting the length of elastic material (14) relative to the backing material (18) for a bonding operation. Ultrasonic horns (104,106) bond the length of elastic material (14) to the backing material (18). The applicator assembly (12) includes rolls (32,36) for tensioning the elastic material (14) and a vacuum mechanism for selectively retaining the length of tensioned material (14) and releasing the tensioned elastic material (14) to the bonding template (16). A mechanism is provided for transferring the tensioned elastic material (14) from the applicator assembly (12) to the bonding template (16) while maintaining the elastic material (14) in the tensioned condition.

24 Claims, 9 Drawing Sheets

METHOD AND APPARATUS FOR APPLYING DISCREET ELASTIC STRIPS TO A STATIONARY WEB

TECHNICAL FIELD

The present invention relates to a method and apparatus for securing an elastic ribbon in a stretched condition to a relatively stationary backing material or web in the manufacture of garments.

BACKGROUND ART

Garments such as disposable diapers include elastic waist or leg bands. The bands are constructed of an elastic ribbon material bonded to a backing material, commonly referred to as a web, such as an elastomeric nonwoven fibrous material. The bonding has been commonly accomplished by either sewing, heat activated coating on the elastic, or by the use of a separate adhesive.

The web material is relatively inelastic compared to the elastic ribbon. Commonly, the elastic material is stretched and then bonded to the web. The following patents relate to methods and apparatus for attaching discreet stretched elastic strands to portions of a web backing material. U.S. Pat. Nos. 4,642,150 to Stemmler, issued Feb. 10, 1987; 4,081,301 to Buell, issued Mar. 28, 1978; 4,504,539 to Petracek et al, issued Mar. 12, 1985; 4,353,762 to Bouda, issued Oct. 12, 1982; 4,364,787 to Radzins, issued Dec. 12, 1982; 4,464,217 to Dickover et al, issued Aug. 7, 1984; 4,479,836 to Dickover et al, issued Oct. 30, 1984; 4,525,229 to Suzuki et al, issued June 25, 1985.

The Stemmler patent shows an applicator including a supply roll for receiving and sizing elastic ribbon drawn from a supply stock. The supply roll holds the elastic tapes by a vacuum mechanism and delivers the tape to an applicator roll where the tape is stretched. The stretched elastic tape which is held on the surface of the applicator roll by a vacuum is then transferred to a web surface for bonding by an adhesive.

The Buell patent discloses the stretching of an elastic ribbon to a desired value by adjusting the speed of the rolls through which the elastic ribbon is guided before proceeding to a bonding station where the stretched elastic is adhesively bonded to a web backing material.

The Petracek et al patent discloses ultrasonic bonding of fibers and yarns to a nonwoven web surface.

Problems arise in effectively transferring a stretched elastic member to a position adjacent the web backing material for bonding. The elastic material must be maintained in a predetermined tensioned state while being positioned relative to and brought in contact with the web for a bonding operation.

It is further desirable to utilize an apparatus that can apply a stretched elastic member to a web backing in either a straight line or in a curved pattern while maintaining the elastic material in the predetermined tensioned state.

It is further preferable to utilize ultrasonic bonding to bond the elastic material to the web backing support. Ultrasonic bonding is capable of delivering a high bonding energy in a shorter period of time with less bond registration variations, resulting in a more accurate and efficient process when compared to thermal bonding. With respect to bonding the preferred materials of the nonwoven fibrous web, ultrasonic bonding enables penetration of the web by the ultrasonically generated frictional heat, melting the polymeric fibers of the web better than thermally generated bonds. Autogenous bonding, that is, ultrasonic or thermal bonding, requires compatible melt temperatures of those polymers comprising the materials sought to bonded together.

The present invention provides an efficient mechanism for ultrasonically bonding a stretched elastic material to a web backing material. The present invention further provides an efficient means for transferring a stretched elastic material to a anvil for ultrasonic bonding while maintaining the elastic material in the stretched condition.

STATEMENT OF THE INVENTION

The present invention provides an apparatus for applying an elastic material to a backing material, the apparatus including applicator means for applying a length of the elastic material to a bonding support means, bonding support means for supporting the length of elastic material relative to the backing material for a bonding operation, and bonding means for bonding the length of elastic material to the backing material. The applicator means includes tensioning means for applying a tension to the length of elastic material and retaining means for selectively retaining the length of tensioned elastic material and releasing the length of tensioned elastic material to the bonding support means.

The present invention further provides a method of applying an elastic material to a backing material, the method including the steps of placing the length of elastic material under tension, applying the length of elastic material to a bonding support surface while maintaining the elastic material in tension, and bonding the length of tensioned elastic material to the backing material.

FIGURES IN THE DRAWINGS

Other advantages of the present invention will be readily appreciated as the same becomes better understood by reference to the following detailed description when considered in connection with the accompanying drawings wherein:

FIG. 8b is an enlarged fragmentary cross sectional view of the highlighted portion of FIG. 9a;

DETAILED DESCRIPTION OF THE INVENTION

Figure 1:
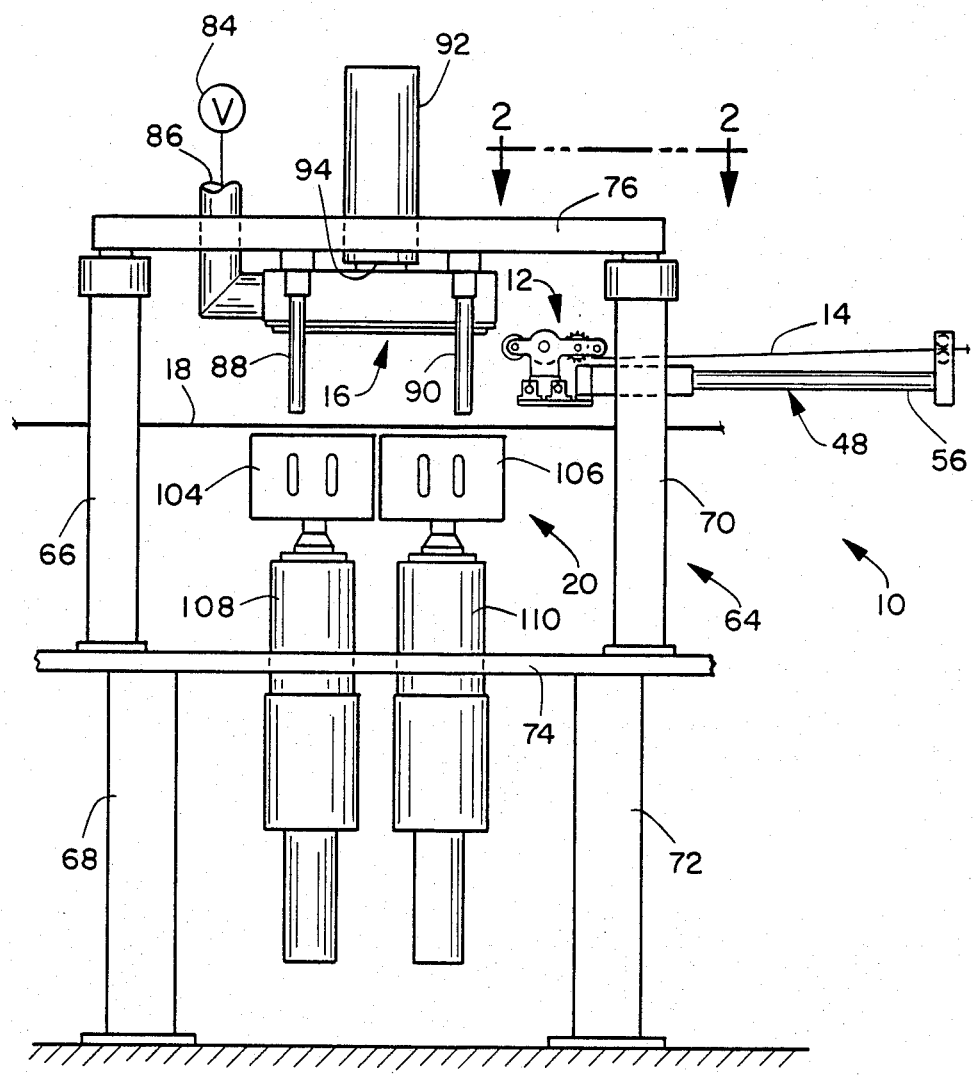
FIG. 1 is an elevational view of the present invention.

An apparatus for applying an elastic material to a backing material is generally shown at 10 in the Figures. The apparatus 10 generally includes applicator means generally indicated at 12 for applying a length of elastic material 14 to a bonding support plate, bonding support means generally indicated at 16 for supporting the length of elastic material 14 relative to a backing material 18 for a bonding operation, and bonding means generally indicated at 20 for bonding the length of elastic material 14 to the backing material 18.

One aspect of the present invention provides the applicator means 12 with tensioning means for applying a tension to the length of elastic material 14 and retaining means for selectively retaining the length of tensioned elastic material 14 and releasing the length of tensioned elastic material 14 to the bonding support means 16. More specifically, the applicator means 12 includes a pair of roll assemblies 22,24 shown in FIG. 2, for simultaneously applying two lengths of the elastic material 14 to the bonding support means 16. Each of the applicator roll assemblies 22,24 includes a drive roll 26 operatively connected through gears 28 and 30 to a tensioning roll 32.

The tensioning means includes the drive roll 26 which has a predetermined diameter and the tensioning roll 32 operatively driven by the drive roll through the gearing 28,30, the tensioning roll 32 having a smaller diameter than the drive roll 26. The assembly 10 includes stay roll 36 positioned adjacent the tensioning roll 32, the tensioning roll 32 imparting a preselected tension to the elastomeric material 14 held between the tensioning roll 32 and stay roll 36 as the elastic material 14 is drawn by the drive roll 26 as described below.

The assembly 10 further includes a guide roll 39 adjacent the drive roll 26, opposite the tensioning roll 32. The stay roll 30 and guide roll 39 each are rotatable in only one direction, that is, when the applicator roll assembly 12 is operated, the stay roll 36 and guide roll 39 rotate with the clockwise movement of the drive roll 26. The stay roll 36 and guide roll 39 prevent the drive roll 26 from rotating in the counterclockwise direction, thereby keeping the elastic material 14 from backing out of the applicator assembly 12 through which the elastic material 14 is threaded.

The retaining means includes a retainer surface 34 on the drive roll 26. The retaining means further includes a vacuum source 43 in communication with a hollow inner core 38 of the drive roll 26 through manifolds 41. Openings 40 extend from the inner core 38 to the retainer surface 34 for operatively conducting the vacuum to the retainer surface 34.

The drive roll 26 includes release means for releasing the elastic material 14 from the vacuum means. The release means includes a plate member 42 fixedly supported within the core 38 of the drive roll 26. The drive roll 26 is rotatable relative to the fixed plate member 42. The plate member 42 is positioned within the inner core 38 adjacent the inner surface of the rotatable drive roll 26 so that the plate member 42 covers the adjacent ones of the openings 40 as the drive roll rotates, the plate member 42 thereby blocking the vacuum to the ones of the openings 40 to release the elastic material 14 from the respective retaining surface 34. As oriented in the Figures, the openings or vacuum apertures 40 are blocked off by the plate member 42 from about the 12 o'clock to about the 3 o'clock positions, resulting in the vacuum being applied by the drive roll 26 to the elastic material 14 where the openings 40 are not blocked, and releasing the elastic material 14 from the retaining surface 34 where the openings 40 are blocked. Thusly, the vacuum through the openings 40 retains the elastic material in the tensioned condition on the retainer surface 34 and the plate member 42 releases the elastic material 14 from the retainer surface 34. In this manner, the applicator assembly 12 provides means which first places the elastic material 14 in tension and then retains the elastic material in the preselected tension until it is released from the drive roll 26.

The applicator assembly 12 is mounted on a support 44. The applicator assembly 12 applies the discrete length of material 14 onto the bonding template 16 as the applicator assembly 12 is moved between a retracted and an extended position. The assembly 12 includes tracking means for tracking the assembly 12 along a curvalinear path between the two positions as the assembly 12 applies the material 14 along the path. The tracking means is universally adjustable to follow either a curved path or straight line path during the application procedure.

The support 44 is a slide block seated for sliding movement on a pair of rods 47,49. The rods 47,49 are mounted on an end portion 46 of an arm assembly generally indicated at 48. The rods 47,49 are secured to the end portion 46 by fastening portions 50.

The arm assembly 48 provides the assembly 10 with applicator extending and retracting means for extending and retracting the applicator means 12 relative to the bonding support means 16 as the applicator means releases and transfers the length of tensioned elastic material 14 to the bonding support means 16. The extension and retraction can occur over a curved or straight line path.

The extending and retracting means includes a retractable arm assembly comprising a plurality of arms 56 connected at joints 58,60,62 and drive means for moving the arm assembly 48 along an infinite path directing the applicator means 12 on a selected path adjacent the bonding support means 16. The arm assembly 48 is mounted on the assembly support structure generally indicated at 64 and is retractable relative to the support structure 64 to remove the applicator means 12 from between the bonding support means 16 and the bonding means 20.

Figure 2:
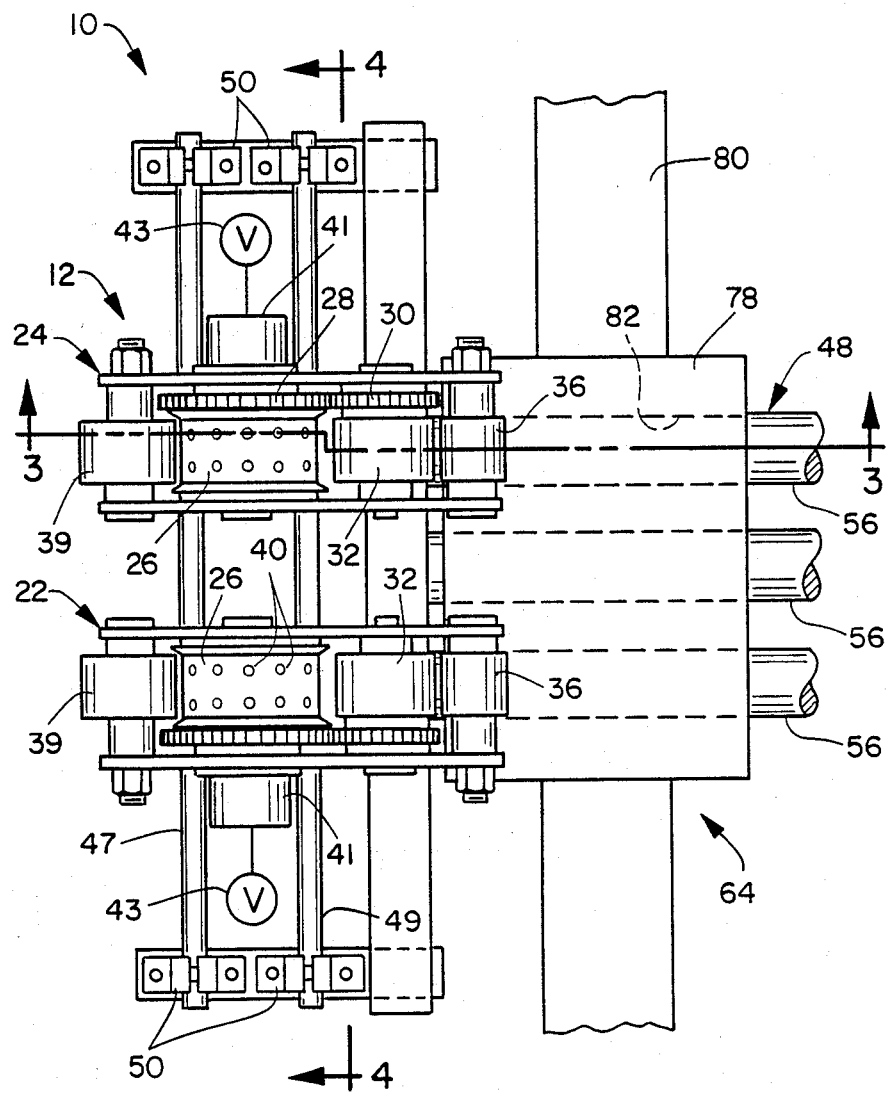
FIG. 2 is an enlarged plan view taken substantially along lines 2—2 of FIG. 1.
Figure 3:
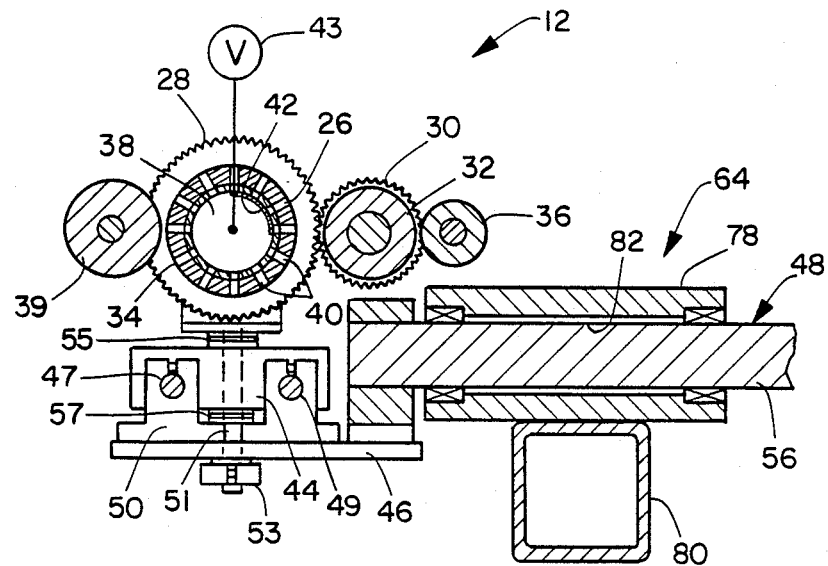
FIG. 3 is a cross sectional view taken substantially along lines 3—3 of FIG. 2.
Figure 4:
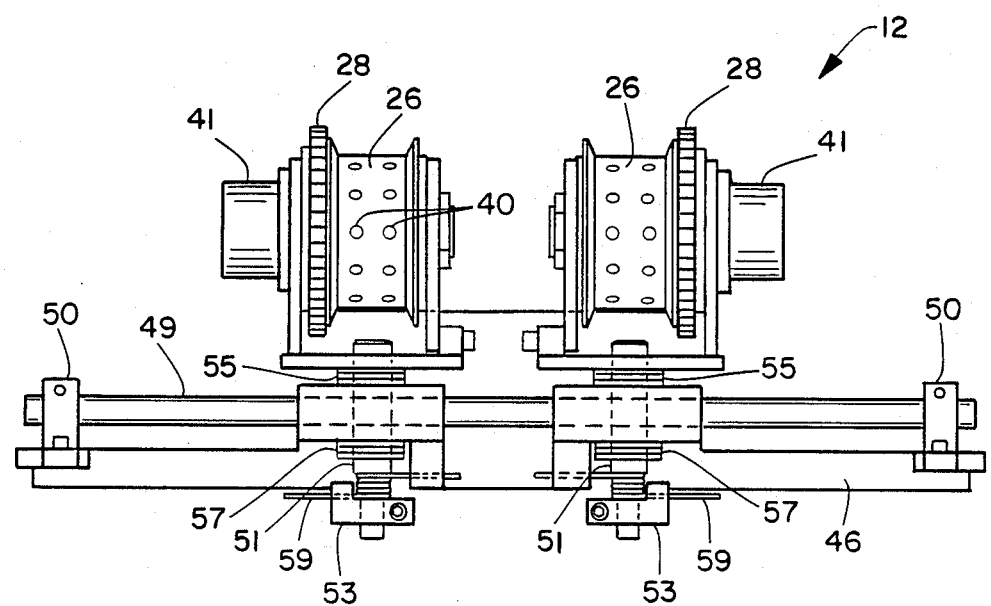
FIG. 4 is a view taken substantially along lines 4—4 of FIG. 2.
Figure 5:
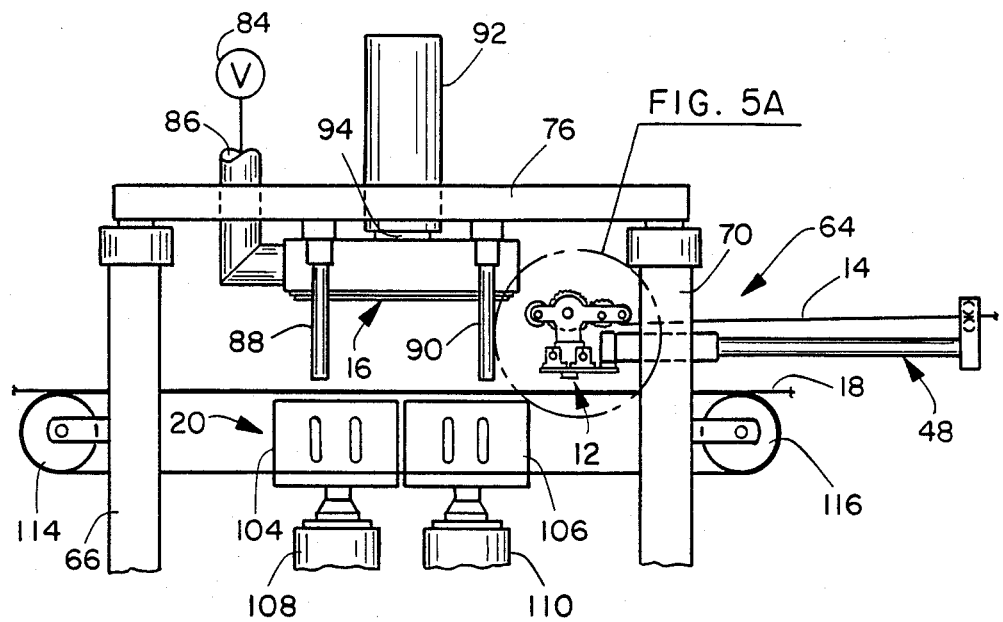
FIG. 5 is a fragmentary elevational view of the present invention highlighting the applicator means in the retracted position.
Figure 5A:
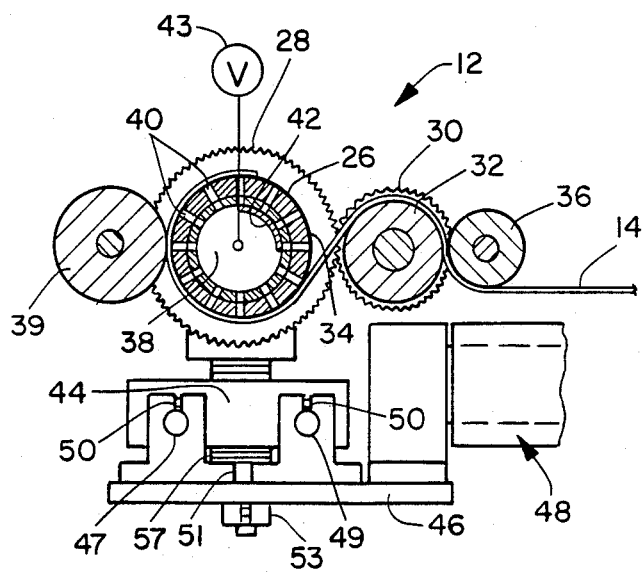
FIG. 5a is an enlargement of the applicator means in the retracted position highlighted in FIG. 5.

The support structure 64 includes a plurality of vertically extending support posts 66,68,70,72 and a plurality of horizontally disposed supports 74,76. The arms 56 are guided through a guide housing 78 mounted on a horizontally disposed support beam 80. The housing 78 includes openings 82 therethrough through which the arms 56 extend. As shown in FIG. 2, the arm assembly 48 may include a plurality of arms 56 supporting the applicator 12.

The bonding support means 16 comprises a bonding template 16 connected to a vacuum source 84 through manifold 86. The bonding template 16 is moveable along guides 88,90 in a vertical direction by extension and retraction means 92. The extension and retraction means 92 can be a hydraulic mechanism comprising a fluid cylinder 92 for driving retractable and extendable piston 94 operatively connected to the bonding template 16.

Figure 9:
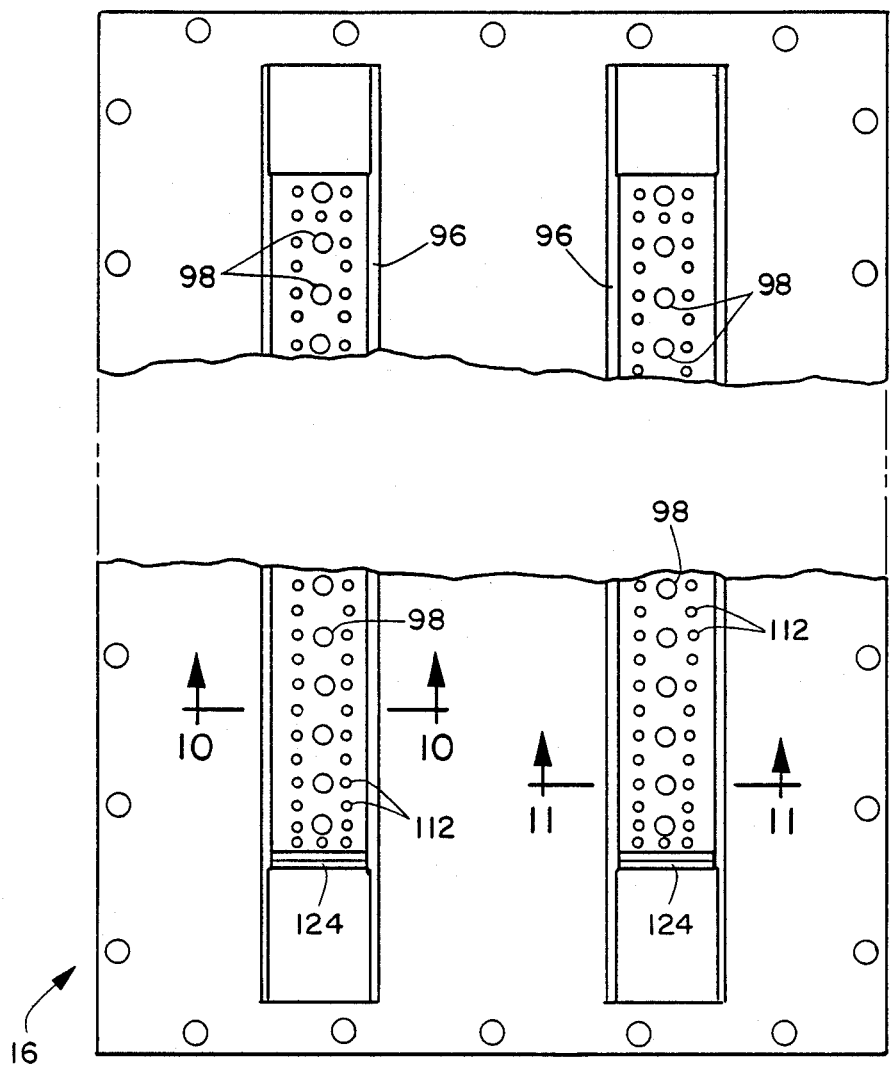
FIG. 9 is a plan view of the bonding support plate.
Figure 10:
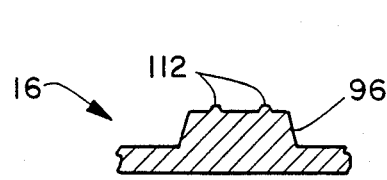
FIG. 10 is a fragmentary cross sectional view taken substantially along lines 10—10 of FIG. 8.
Figure 11:
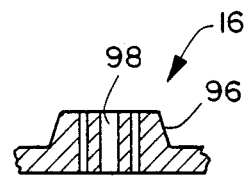
FIG. 11 is fragmentary cross sectional view taken substantially along line 11—11 of FIG. 9.

The bonding template 16 includes a pair of raised support paths 96. The support paths 96 may be linear, as shown in FIG. 9 at 96 or may be curvalinear as shown at 96' in FIG. 13. Each support path 96,96' defines a path onto which the length of the tensioned elastic material 14 is transferred.

The tracking means of the applicator means 12 includes follower means for following the paths 96,96' as the elastic material 14 is transferred from the applicator means 12 to the path 96,96'. More specifically, the raised support path 96,96' is a raised surface including holding means for holding the length of the tensioned elastic material 14 in the tensioned condition once it is transferred from the applicator assembly 12. The holding means includes the vacuum source 84 which is in communication with the raised surfaces 96,96' through openings 98. The vacuum selectively holds the length of tensioned elastic material 14 against the raised surfaces 96,96' and maintains the elastic material 14 in the tensioned condition upon transfer from the applicator means 12.

Figure 12:
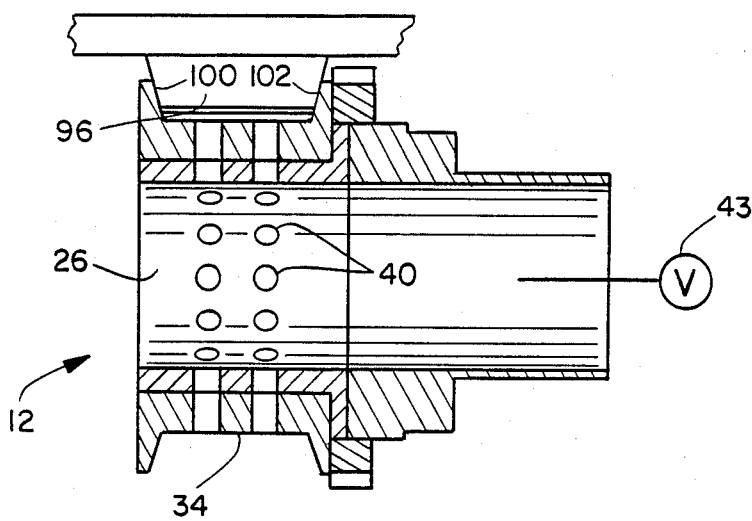
FIG. 12 is a side elevational view of the drive roll of the applicator means in frictional contact with the raised portion of the bonding template.

The follower means of the applicator assembly 12 includes the annular recessed surface 34 of the drive roll 26 and annular walls 100,102 on each side of the recessed surface 34 defining an annual channel for rolling mating engagement with the raised portion 96,96'. The mating engagement is shown in FIG. 12.

The tracking means further includes a universal support for supporting the drive roll 26 through simultaneously forward, lateral, and rotational translation thereof relative to the bonding template 16. The drive roll 26 is mounted on an axle 51 operatively connected to the slide block 44 for rotational movement relative thereto. Fasteners 53 and bearings 55,57 connect the axle 51 to the block 44. Spring 59 biases the axle 51 and connected drive roll 26 to a neutral position. In the neutral position, the drive roll 26 is positioned to initially matingly engage the origin of the raised portion 96,96'.

Figure 13:
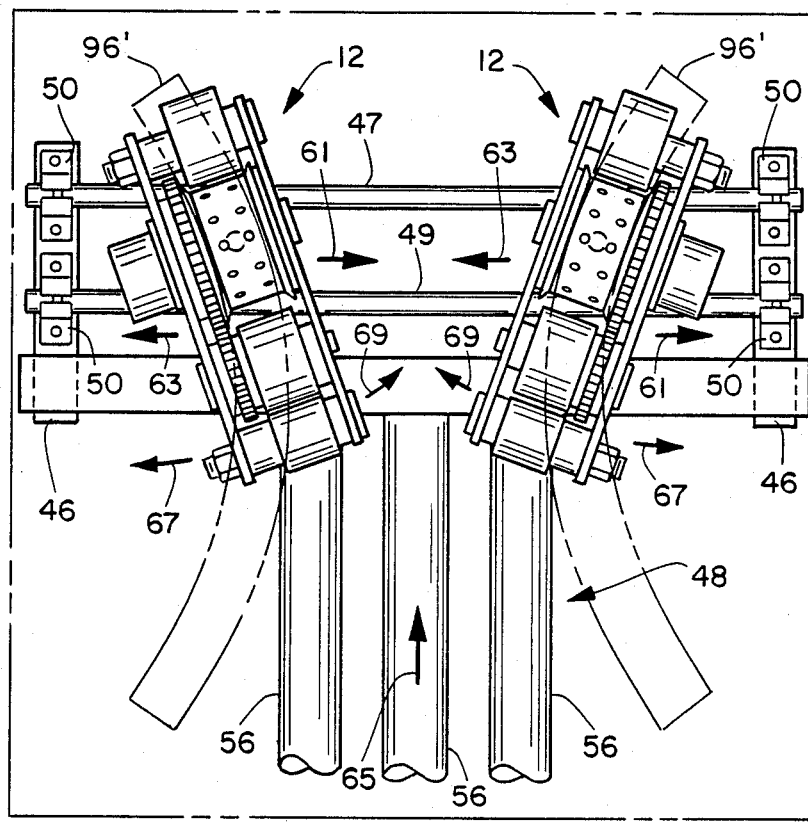
FIG. 13 is a plan view showing the applicator means on the raised portion schematically shown as dash lines.

In operation, the arm assembly 48 extends the applicator assembly 12 so that the drive rolls 26 engage the origin of the tracks 96,96'. As shown in the Figures, the applicator assembly 12 includes a pair of drive rolls 26. The drive rolls 26 are in the neutral position, as shown in FIG. 2 wherein the rolls 26 track in a direction substantially perpendicular to the rods 47,49. When the applicator assembly 12 is used with a bonding template 16 as shown in FIG. 9, wherein the template 16 includes straight tracks 96, the recessed portion 34 ride on and engage the raised portions 96 and follow the straight line thereof. As shown in FIG. 13, as the applicator assemblies 12 engage and follow a curved track 96', the applicator assemblies 12 translate laterally as shown by arrows 61,63 along the rods 47,49. The applicator assembly 12 translates in the forward direction, as indicated by arrows 65 by extension of the arm assembly 48. The applicator assemblies 12 translate rotationally as indicated by arrows 67,69 by rotation of the axles 51. Accordingly, the combination of the connection of the applicator assemblies 12 to the rods 47,49, to the axles 51, and to the arm assembly 48 provides for universal forward, lateral, and rotational movement of the applicator assemblies 12 so that they can follow an infinite variety of curvalinear paths. Thus, the present invention provides an applicator assembly which can apply a discrete length of elastic material to a bonding template, and eventually to a backing material, in an infinite variety of forms.

The bonding means 20 includes a pair of ultrasonic horns 104,106, each horn 104,106 supported on a hydraulic actuator 108,110, respectively for actuating vertical movement of the horns 104,106. The raised surfaces 96,96' include metallic projections 112 defining anvil means for cooperating with the ultrasonic horns 104,106 to bond the tensioned elastic material 14 to the backing material 18 by ultrasonic bonding as discussed below.

The support structure includes roll supports 114,116 for supporting rolls of backing material sheets 18 on a path between the bonding template 16 and the ultrasonic horns 104,106. The support structure 64 supports the bonding support means 16 and ultrasonic horns 104,106 for reciprocating movement towards and away from the path of the sheet of backing material 18 when the applicator means 12 retracted to thereby sandwich the backing material 18 between the bonding template 16 holding the length of tensioned elastic material 14 and the ultrasonic horns 104,106.

The backing material 18 is an elastomeric nonwoven fibrous material, carried either on a tentered frame or a vacuum belt which supports the backing material under minimal tension along the opposed margins thereof and in the stationary position relative to the bonding template 16 and ultrasonic horns 104,106.

The present invention further provides a method of applying the elastic material 14 to the backing material 18, the method generally including the steps of placing the length of elastic material 14 under a predetermined tension, applying a length of elastic material 14 to the bonding support surface 16 while maintaining the elastic material 14 in tension, and bonding the length of tensioned elastic material 14 to the backing material 18.

More specifically, and as illustrated through the sequential drawings in FIGS. 2 through 8a, the elastic material 14 is threaded from a source (not shown in the drawings) through between the tensioning roll 32 and stay roll 36, around the drive roll 26 between the guide roll 39 and held on the drive roll 26 beyond the guide roll 39 by the vacuum mechanism 43 through the manifold 41.

Figure 6:
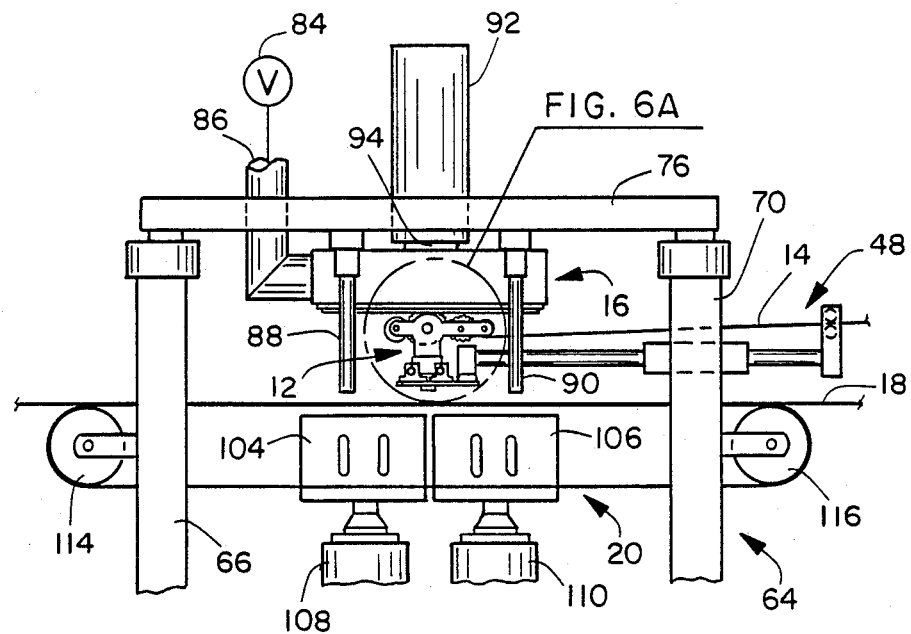
FIG. 6 is an elevational view of the present invention highlighting the applicator means applying a length of tensioned elastic material to the bonding support plate.
Figure 6A:
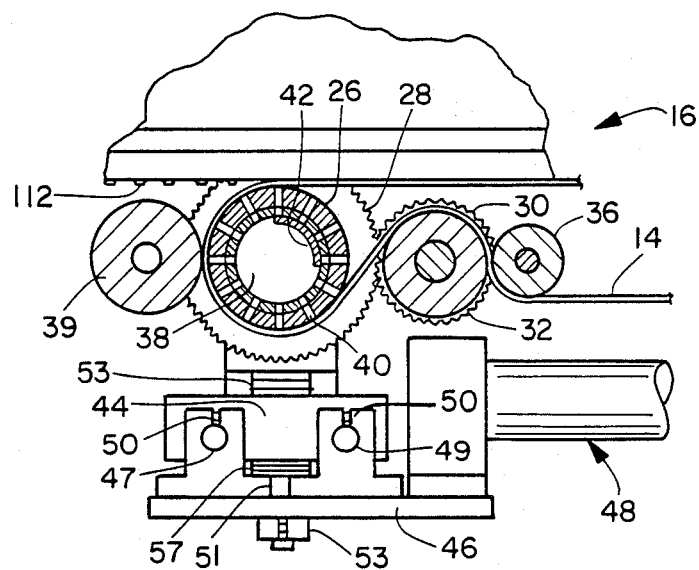
FIG. 6a is an enlargement of the highlighted portion in FIG. 6.
Figure 7:
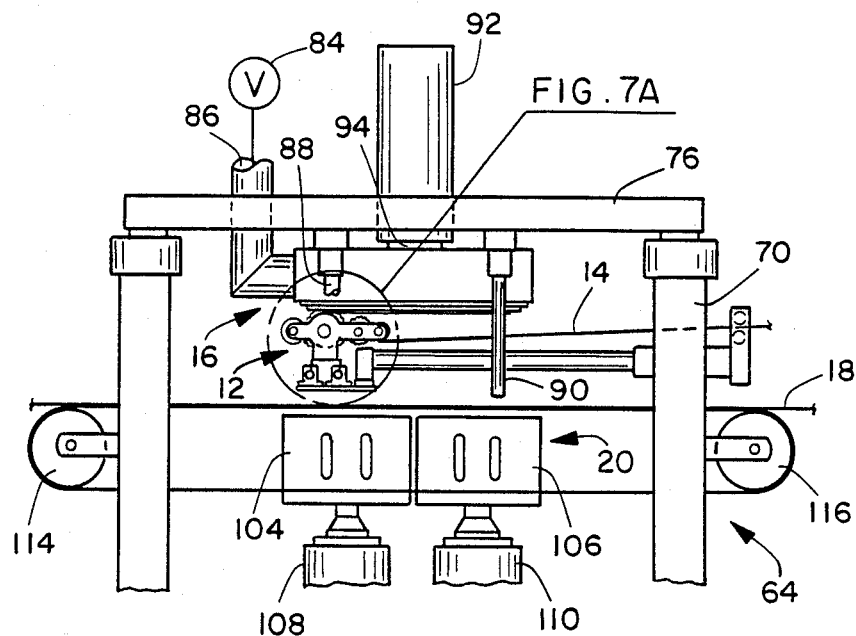
FIG. 7 is an elevational view highlighting the applicator means fully extended relative to the bonding support plate.
Figure 7A:
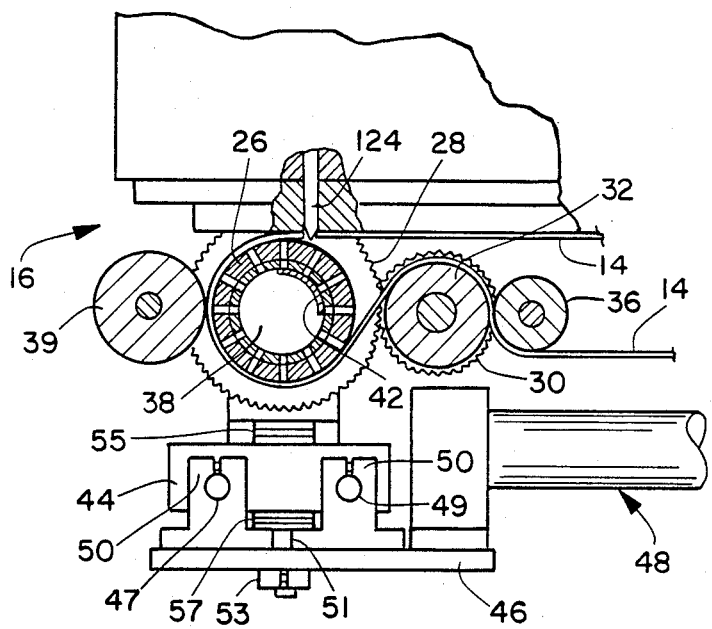
FIG. 7a is the highlighted portion of FIG. 7.

The arm assembly 48 extends the applicator assembly 12 so that the drive roll 26 is moved adjacent to the raised portion 96 on the bonding support surface 16. The elastic material 14 which is in the tensioned condition as it is threaded around the drive roll 26 and maintained thereby by the vacuum communicated through the openings 40 is sandwiched between the drive roll 26 and raised surface 96,96'. The drive mechanism of the arm assembly 48 moves the applicator assembly 12 so that the frictional engagement of the drive roll 26 against the bonding support surface 16 rotates the drive roll 26. As the drive roll 26 rotates the elastic material 14 is drawn from between the tension roll 32 and stay roll 36 and about the drive roll 26 and fed onto the raised surface 96,96'. As shown in FIG. 6a, the elastic material 14 is held on the drive roll 26 by the vacuum through the openings 40 until the elastic material is both in contact with the raised portion 96 and the adjacent opening 40 is covered by the plate member 42. At this point, there is no longer a vacuum holding the elastic material 14 on the drive roll 26 and the vacuum communicated through the openings 98 maintains the tensioned elastic material 14 on the raised portion 96 in the tensioned condition. In other words, the transfer of the tensioned elastic material is perfected through the combination of the vacuum means through the drive roll 26 being excommunicated by the plate member 42 coincidently with the tensioned elastic material 14 coming into contact with the vacuum effected through the openings 98 in the raised surface 96 of the template surface 16.

As the applicator assembly 12 reaches the end of the raised portion 96, a knife mechanism 124 cuts the length of elastic material 14 thereby leaving on the raised portion 96 a predetermined length of elastic material 14 which is in a tensioned condition and in a predetermined configuration.

Figure 8:
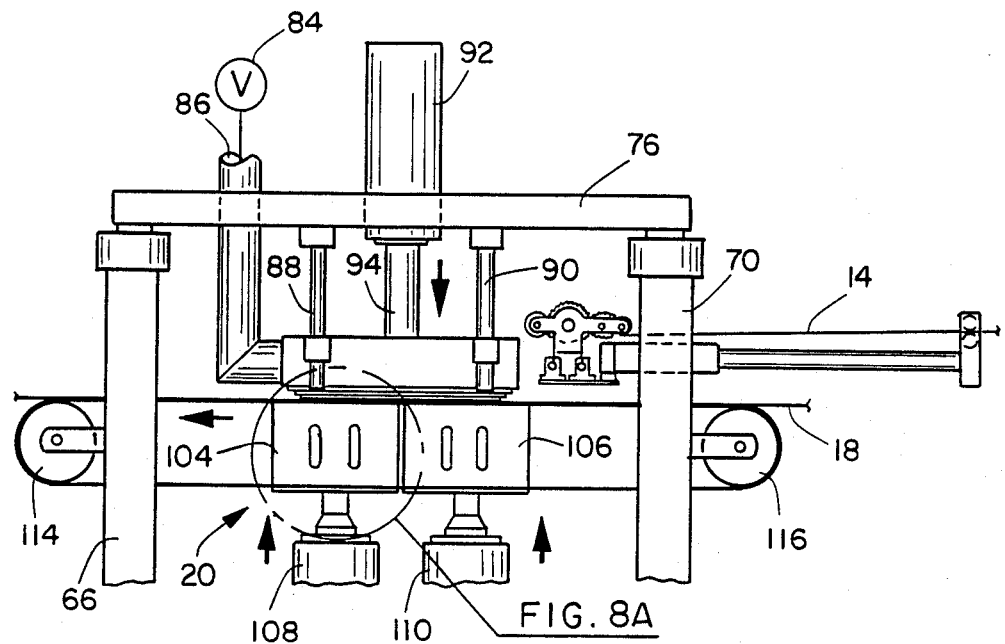
FIG. 8 is an elevational view of the present invention highlighting the bonding support plate brought into proximity of the backing material and the ultrasonic horns brought into contact with the other side of the backing material.
Figure 8A:
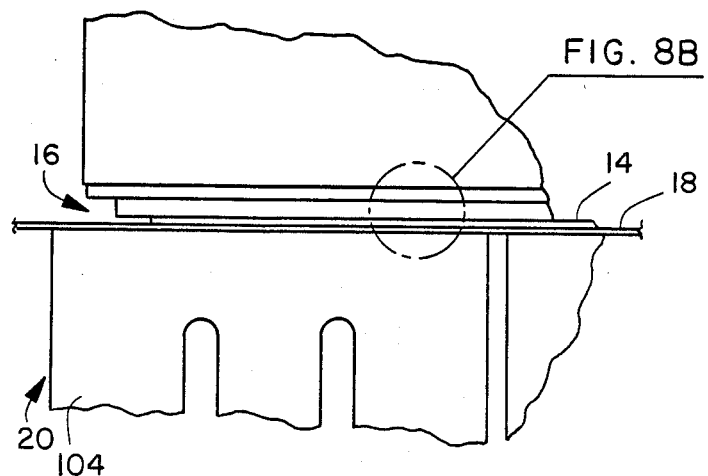
FIG. 8a is an enlarged fragmentary elevational view of the highlighted portion of FIG. 8 highlighting the bonded materials between the anvil and ultrasonic horn.
Figure 8B:
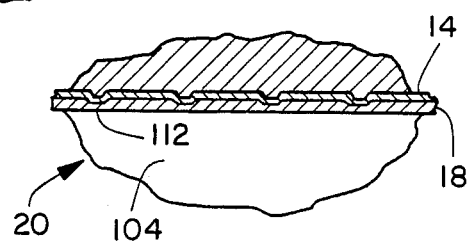

As shown in FIGS. 8 and 8a, the applicator assembly 12 is retracted to a position which is no longer between the bonding support means 16 and the bonding means 20. The backing material 18 is led from roll 114 to 116 and is held relatively stationary relative to the disposed tensioned elastic material 14. In order to bond the tensioned elastic material to the backing material 18, the hydraulic mechanism 92 lowers the bonding support plate 16 so that the tensioned elastic material comes in contact with the backing material 18. Concurrently, the hydraulic mechanisms 108,110 raise the ultrasonic horns 104,106, respectively, to contact the backing material 18 from the opposite side. The raised projections 112 function as an ultrasonic bonding anvil when the tensioned elastic material 14 is held poised on the projections 112 and brought into contact with the stationary elastomeric backing material 18 during activation of the ultrasonic horns 104,106. After the materials 14 and 18 are bonded together, the ultrasonic horns 104,106 are lowered. The bonding template 16 is raised leaving the tensioned elastic material on the backing material. The rollers 114,116 are moved to dispose a new length of backing material 18 between the bonding template 16 and ultrasonic horns 104,106 and the process is repeated.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. An apparatus (10) for applying an elastic material (14) to a backing material (18), said apparatus (10) comprising:

bonding support means (16) for supporting a length of the elastic material (14) relative to the backing material (18) for a bonding operation;

bonding means (20) for bonding the length of elastic material (14) to the backing material (18); and an applicator (12) for applying the length of elastic material (14) to the bonding support means (16), including a drive roll (26) having a predetermined diameter, a tensioning roll (32) operatively driven by said drive roll and having a smaller diameter than said drive roll (26), a stay roll (36) positioned adjacent said tensioning roll (32), said tensioning roll (32) imparting a preselected tension to the elastic material (14) held between said tensioning roll (32) and said stay roll (36) as the elastic material (14) is drawn by said drive roll (26) from between said tensioning roll (32) and stay roll (36), and wherein said drive roll (26) includes a retainer surface (34) and an inner core (38) including vacuum means, said retainer surface including openings (40) therethrough for operatively conducting the vacuum to said retainer surface (34), whereby the tensioned elastic material (14) is held for transfer to said bonding support means (16) in the tensioned condition.

2. An apparatus as set forth in claim 1 wherein said drive roller (26) includes release means for releasing the elastic material (14) from said vacuum means.

3. An apparatus as set forth in claim 2 wherein said release means includes a plate member (42) fixedly supported within said inner core (38) of said drive roll (26), said drive roll (26) including an outer portion including said retainer surface (34), said outer portion being rotatable relative to said plate member (42), said plate member (42) covering the adjacent ones of said openings (40) as said outer portion rotates to block the vacuum to said ones of said openings (40) to release the elastic material (14) from the respective retaining surface (34).

4. An apparatus as set forth in claim 1 including applicator extending and retracting means for extending and retracting said applicator (12) relative to said bonding support means as said retaining means releases and transfers the length of tensioned elastic material (14) to said bonding support means (16).

5. An apparatus as set forth in claim 4 wherein said extending and retracting means includes a retractable arm and arm drive means for moving said arms (48) and directing said applicator means (12) on a selected path adjacent said bonding support means (16).

6. An apparatus as set forth in claim 5 wherein said arms (48) are mounted on a support structure (64) and retractable relative to said support structure (64) to remove said applicator (12) from between said bonding support means (16) and said bonding means (20).

7. An apparatus as set forth in claim 4 wherein said bonding support means (16) includes a support path (96,96') defining a path onto which the length of tensioned elastic material (14) is transferred, said applicator (12) including follower means for following said path (96,96') as the elastic material (14) is transferred from said applicator (12) to said path (96,96').

8. An apparatus as set forth in claim 7 wherein said support path (96,96') includes a raised surface (96,96'), said raised surface (96,96') including holding means for holding the length of tensioned elastic material (14) in the tensioned condition, said follower means including an annular recessed surface (34) of said drive roll (26) and an annular wall (100,102) on each side of said recessed surface (34) defining an annular channel for rolling mating engagement with said raised surface (96,96'), said recessed surface (34) including said support surface (34) of said applicator (12).

9. An apparatus as set forth in claim 8 wherein said holding means includes second vacuum means (84) for effecting a vacuum and openings (98) through said raised surface (96,96') for conducting the vacuum from said second vacuum means (84) to said raised surface (96,96') to selectively hold the length of tensioned elastic material (14) against the raised surface (96,96') and maintain the elastic material (14) in the tensioned condition.

10. An apparatus as set forth in claim 8 wherein said bonding means (20) includes an ultrasonic horn (140,106), said bonding support means including anvil means for cooperating with said ultrasonic horn (104,106) to bond the tensioned elastic material (14) to the backing material (18) by ultrasonic bonding.

11. An apparatus as set forth in claim 10 wherein said raised surface (96,96') comprises projections (112) defining said anvil means.

12. An apparatus as set forth in claim 6 wherein said support structure (64) includes a pair of roll supports (114,116) for supporting a sheet of backing material (18) on a patch between said bonding support means (16) and said ultrasonic horn (104,106), said support structure (64) supporting said bonding support means (16) and said bonding means (20) for reciprocating movement towards and away from the path of the sheet of backing material (18) when said applicator (12) is retracted to sandwich the backing material (18) between the bonding support means (16) holding the length of tensioned elastic material (14) and the bonding means (20).

13. An apparatus as set forth in claim 1 wherein said bonding support means (16) includes holding means for holding the length of tensioned elastic material (14) transferred from said applicator (12) means in the tensioned condition.

14. An apparatus (10) for applying an elastic material (14) to a backing material (18), said apparatus (10) comprising: bonding support means (16) for supporting the length of elastic material (14) relative to the backing material (18) for a bonding operation; bonding means (20) for bonding the length of elastic material (14) to the backing material (18); a support structure (64) including a pair of roll supports (114,116) for supporting the backing material (18) on a path between said bonding support means (16) and said bonding means (20); an applicator (12) for applying a length of the elastic material to said bonding support means (16); and applicator extending and retracting means (48) for extending and retracting said applicator (12) in a plane generally parallel to and between said bonding support means (16) and said bonding means (20) as said applicator (12) releases and transfers the length of elastic material (14) to said bonding support means (16).

15. An apparatus as set forth in claim 14 wherein said extending and retracting means includes a retractable arm and arm drive means for moving said arms (48) and directing said applicator (12) on a selected path adjacent said bonding support means (16).

16. An apparatus as set forth in claim 15 wherein said arms (48) are mounted on a support structure (64), said arms (48) being retractable relative to said support structure (64) to remove said applicator (12) from between said bonding support means (16) and said bonding means (20).

17. An apparatus as set forth in claim 14 wherein said support means includes web support means (114,116) for supporting a continuous sheet of backing material (18) on a path between said bonding support means (16) and said bonding means (20), said support structure (64) supporting said bonding support means (16) and said bonding means (20) for reciprocating movement towards and away from the path of the sheet of backing material (18) when said applicator means (12) is retracted to sandwich the backing material (18) between the bonding support means (16) holding the length of tensioned elastic material (14) and said bonding means (20).

18. An apparatus (10) for applying a material (14) to a backing material (18), said apparatus (10) comprising: an applicator (12) movable between a first and second position for applying a discrete length of the material (14) onto a bonding template (16) as said applicator (12) is moved between said first and second positions, said applicator (12) including tracking means for tracking said applicator along a curvalinear path between said first and second positions as said applicator applies the material along said path, including follower means for following a track on the bonding template (16) and universal support means for supporting said follower means through simultaneous forward, sideways, and rotational translation thereof relative to said bonding template (16).

19. An apparatus as set forth in claim 18 wherein said applicator includes a drive roll (26), said follower means including an annular recessed surface (34) of said roll (26) and an annular wall (100,102) on each side of said recessed surface (34) defining an annular channel for mating engagement with a curvalinear raised surface (96,96') on the bonding template (16).

20. An apparatus as set forth in claim 19 wherein said universal support means includes a pair of parallel rod members (47,49) and a slide block member (44) mounted on said rod members (47,49) for sliding movement therealong and swivel connector means operatively connecting said drive roll (26) to said slide block member (44) for swiveling movement of said drive roll (26) relative to said slide block member (44).

21. A method of applying
   an elastic material (14) to a backing material (18) for performing a bonding operation said method including the steps of: placing a length of the elastic material (14) under tension by drawing an elastic material (14) between a pair of tensioning rolls (33,36) to apply a uniform preselected tension to the length of elastic material (14); holding the length of elastic material (14) in the tensioned condition by extending the tensioned elastic material (14) around a drive roll (26); maintaining the elastic material (14) in tension on the drive roll (26); moving the drive roll (26) along a bonding support surface (16) as the elastic material (14) is sandwiched between the drive roll (26) and bonding support surface (16); releasing the elastic material (14) from the drive roll (26) as it contacts the bonding support surface (16), while maintaining the elastic material (14) transferred to the bonding support surface (16) under the same tension; cutting the length of the tensioned elastic material (14); and retracting the drive roll (26) relative to the bonding support surface (16).

22. A method as set forth in claim 21 further comprising the step of transferring the length of tensioned elastic material (14) from the drive roll (26) to the bonding support surface (16) including a plurality of openings (98) therethrough and applying a vacuum through the openings to hold the length of elastic material (14) against the bonding support surface (16) in the tensioned condition by the vacuum.

23. A method as set forth in claim 21 further comprising the step of bonding the length of elastic material (14) to the backing material (18) by removing the applicator (12) from between the bonding support surface (16) and an ultrasonic horn; moving the bonding support surface (16) adjacent to one side of a stationary backing material (18) held under minimum tension; moving an ultrasonic horn (104,106) adjacent to the other side of the backing material (18); and utilizing the bonding support surface (16) as an anvil to ultrasonically bond the length of tensioned elastic material (14) to the backing material (918).

24. A method of applying a material (14) to a backing material (18) while stationary, said method including the steps of: applying a discrete length of material (14) from an applicator (12) to a bonding template (16) as the applicator (12) is moved between a first and second position; tracking the applicator (12) along a curvalinear path between the first and second positions as the applicator (12) applies the material (14) along the path wherein said tracking step is further defined as following a drive roll (26) of the applicator (12) along a raised track (96,96') as the drive roll applies the material (14) to the track (96,96').

* * * * *